United States Patent
Gauthier

[19]

[11] Patent Number: 5,819,580
[45] Date of Patent: Oct. 13, 1998

[54] BENDING TOOL

[75] Inventor: Michael T. Gauthier, Oak Creek, Wis.

[73] Assignee: Beere Precision Medical Instruments, Inc., Racine, Wis.

[21] Appl. No.: 58,788

[22] Filed: Apr. 13, 1998

[51] Int. Cl.⁶ ...................................................... B21D 7/06
[52] U.S. Cl. ............................... 72/458; 72/216; 72/217; 72/409.1; 140/106
[58] Field of Search ............................. 72/215, 216, 217, 72/218, 219, 387, 388, 409.09, 409.1, 458; 140/106

[56] References Cited

U.S. PATENT DOCUMENTS

| | | | |
|---|---|---|---|
| 1,824,219 | 9/1931 | Loveless | 72/216 |
| 2,087,125 | 7/1937 | Smith et al. | 140/106 |
| 2,502,713 | 4/1950 | Fagge | 72/388 |
| 2,861,490 | 11/1958 | Rozmus | 72/409.1 |
| 3,126,773 | 3/1964 | Taylor et al. | 81/15 |
| 3,199,549 | 8/1965 | Wallshein | 140/106 |
| 3,709,264 | 1/1973 | Amman | 140/106 |
| 4,304,117 | 12/1981 | Rawson | 72/388 |
| 4,474,046 | 10/1984 | Cook | 72/409 |
| 5,490,409 | 2/1996 | Weber | 72/458 |

*Primary Examiner*—David Jones
*Attorney, Agent, or Firm*—Arthur J. Hansmann

[57] ABSTRACT

A bending tool for bending rods or like items, and including two handles and three bending posts. Two of the posts move with the handle, and the third post is a center post which is selectively rotatable to positions for determining the bend in the item. A pin interconnects the handle and the center post to hold the latter in its selected position during the bending process.

10 Claims, 3 Drawing Sheets

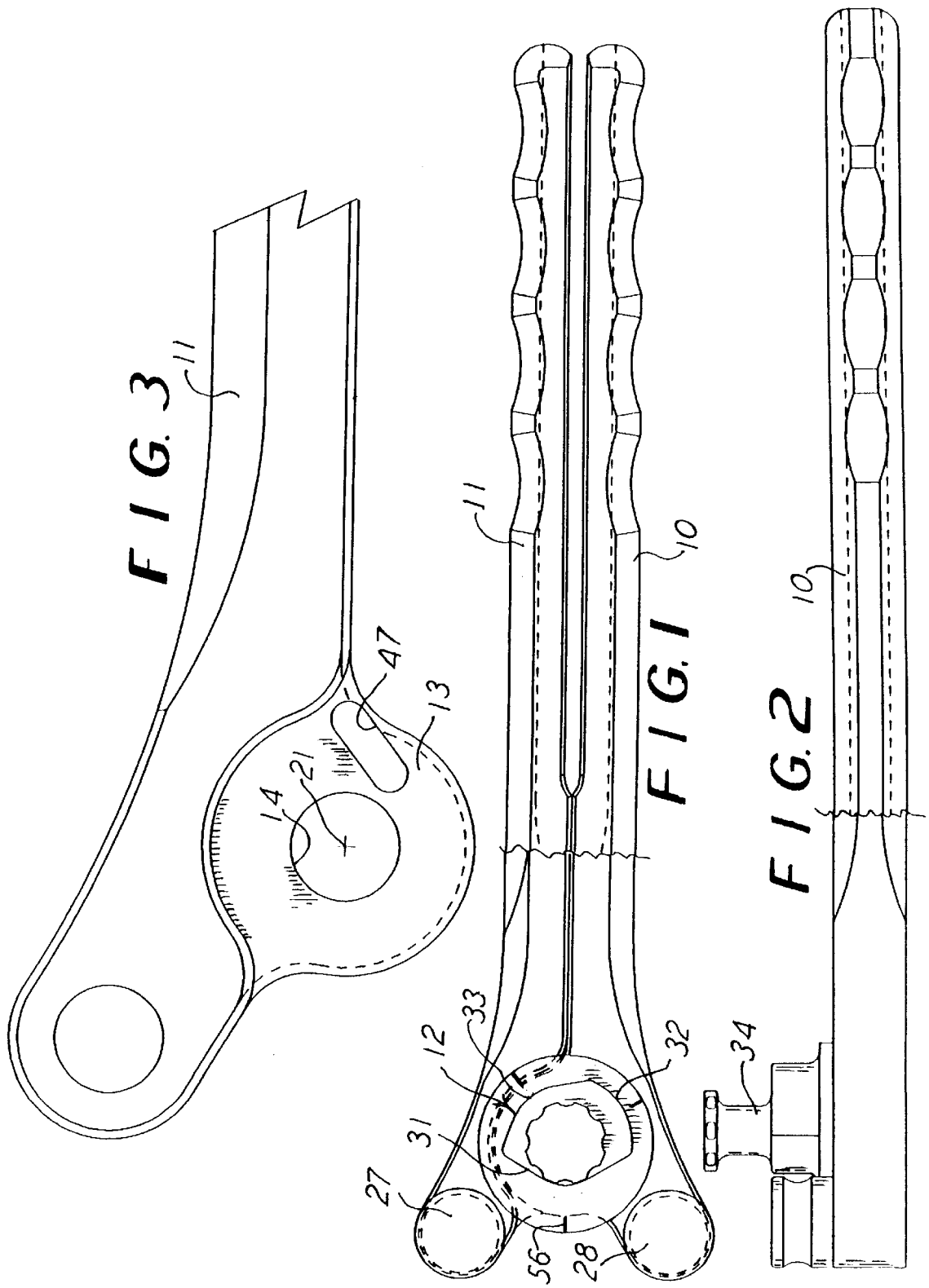

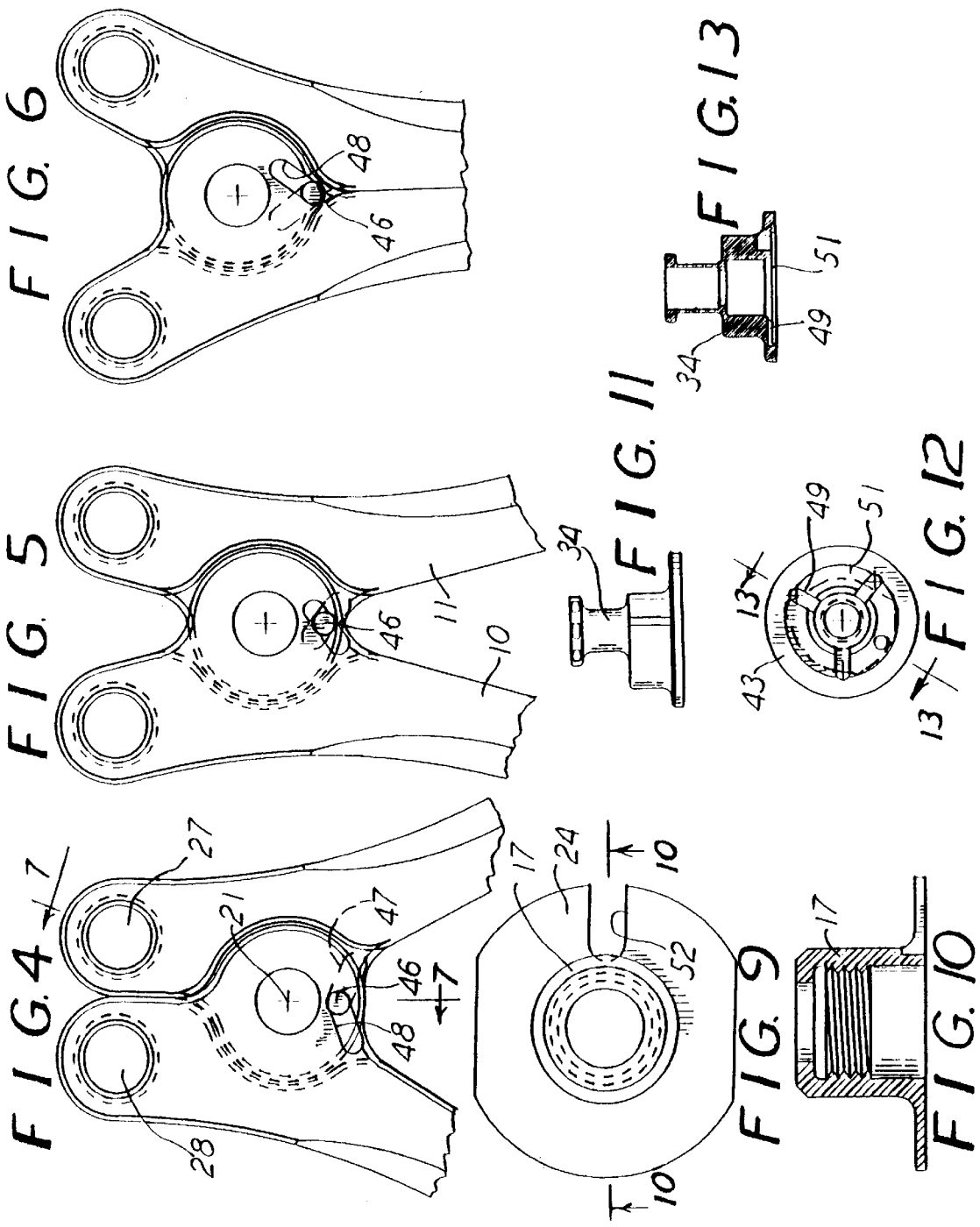

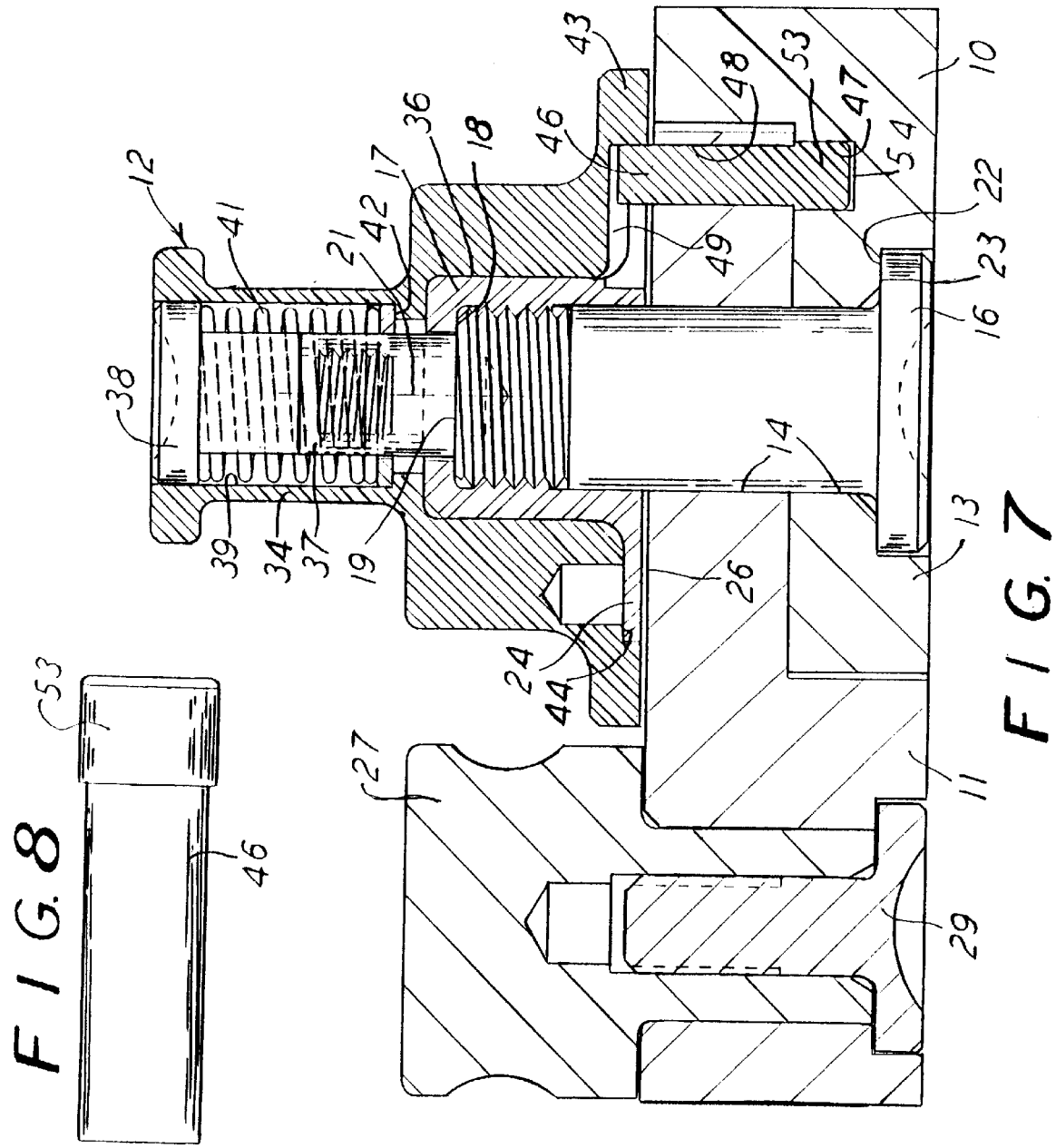

BENDING TOOL

This invention relates to a bending tool, and, more particularly, it relates to a plier-type of tool which is utilized in bending rod or like items, including those useful in surgical implants.

BACKGROUND OF THE INVENTION

Bending tools are already well known in the prior art, and they exist in the form of a plier tool which has two handles which are hand gripped for compressing and moving posts which engage the item to be bent. In sum, there are three posts, two of which move with the pivoting of the handles, and the third of which is a central post located on a fixed axis. That central post is selectively rotatable about its fixed axis and it has different peripheral configurations for presenting different bending surfaces to the rod or item to be bent. In that arrangement, the center post can be maneuvered and rotated and then is field in its rotated position during the bending procedure.

Certain of the prior art is even arranged to have the center bending post held in its selected rotated position by means of a pin which is supportably but articularly connected to the handles. The pin can move in a radially disposed groove in the central bending post to hold the post in its selected rotated position during the bending process.

The present invention improves upon that prior art by arranging the handles, the central post, and the interconnecting pin in a manner which presents the pin directly on the handles and in contact therewith so there are no intervening parts between the pin and the center bending post. In that arrangement, the center bending post is held in its most secure position during the bending, and there are no intervening parts between the pin and the post to permit any wiggling or the like of the post during the bending.

Another object of this invention, and an improvement upon the prior art, is that the pin inter-engaged between the handles and the center post moves radially outwardly on the center post in proportion to the maneuvering of the handles to their closed positions. That is, when the handles are moved to the closed position for the bending process, the greatest force is being applied to all of the posts, and particularly to the center post, and it is during that relationship that the center post is most securely held against any rotation away from its selected rotated position.

Still further, the present invention provides for the accomplishment of the aforementioned and to do so with a sturdy design and one of reliability so that the restraining pin is always positively positioned and is in direct contact with both the handles and the center post.

Still further, the arrangement in this invention is such that the inter-engaging pin is not required to be positively connected to either the handles or to the center post, and it is therefore positioned and at liberty to seek the desired control position of inter-engagement between the handles and the center post.

Rod benders require considerable human-applied forces, and the present invention provides a rod bender which is stable in its pivotal action, that is, in its movement about its pivot post, when subjected to the considerable forces of bending.

BRIEF DESCRIPTION OF THE DRAWINGS

FIG. 1 is a top plan view of a rod bender of this invention, and with the handle shown fore-shortened.

FIG. 2 is a side elevational view of FIG. 1.

FIG. 3 is an enlarged plan view of a fragment of the right-hand handle of FIG. 1.

FIGS. 4, 5, and 6 are plan views of a fragment of the bender seen in FIG. 1, slightly enlarged, and with parts removed and in three positions of bending.

FIG. 7 is an enlarged sectional view taken on the line 7—7 of FIG. 4.

FIG. 8 is an enlarged view of the pin shown in FIG. 7.

FIG. 9 is a top plan view of a retaining nut, such as shown in FIG. 7.

FIG. 10 is a sectional view of FIG. 9, on line 10—10.

FIG. 11 is a side elevational view of the cam of this invention.

FIG. 12 is a bottom plan view of FIG. 11.

FIG. 13 is a sectional view taken on the line 13—13 of FIG. 12.

DETAILED DESCRIPTION OF THE PREFERRED EMBODIMENT

The rod bender of this invention includes two handles 10 and 11 which may be left and right hand handles, respectively. The handles are joined together about a common pivot post generally designated 12. Each handle has a flange portion 13 which defines an opening 14 through which a pivot post bolt 16 extends, as best seen in FIG. 7. The flanges 13 overlap each other and their two openings 14 are aligned and thereby define one opening for snug reception of the pivot bolt 16. A nut 17 is interiorly threaded to receive the threads of the bolt 16. The nut 17 has an angular shoulder 18 which engages a shoulder 19 of the nut 17 and thereby establishes the overall axial or longitudinal length of the bolt 16 and nut 17 relative to securing the two handles 10 and 11 in their axial direction through the openings 14. That is, the nut 17 and bolt 16 define a restricted length there-between, and the two handles 10 and 11 are confined to that length but are permitted to pivot about the axis 21 which is the longitudinal axis through the bolt 16 and through the entire pivot connection for the bender. The bolt 16 has a shoulder 22 which bears against the surface 23 of the underneath handle flange 13, and thus the overall axial dimension along the axis 21 is limited so that there is stability, rather than play or looseness, in the pivot connection for the two handles 10 and 11. That stability is achieved by means of the nut 17 having an annular flange 24 extending therearound and overlapping the upper surface 26 of the top handle. That is, in the pivot connection arrangement described, the bolt shelf 22 and the nut flange 24 restrict movement of the handles along the axis 21 and thus there is stability, though the handles are pivotal. FIGS. 9 and 10 also show the nut 17 and show the flange 24 which extends in a general circular pattern on the nut 17.

The extreme enlarged view of FIG. 7 shows a slight space between the nut flange 24 and the top surface 26 of the handle, and that space is only of a minimal dimension to permit the pivot action, but it does not permit the play or movement of the handles in the direction perpendicular to the pivotal direction of the handles, and thus the stability is achieved.

The previously referred to drawings also show the pair or other two bending posts 27 and 28 which are actually slightly rotatable about their mounting bolts 29 which extend through the respective ones of the handles 10 and 11.

It will of course be understood by one skilled in the art that an item to be bent, such as a rod, will be placed on the bender to extend between the center post 12 and the two posts 27 and 28. Thus, with the bender in the position shown in FIG. 4 and a rod applied thereon, in the manner well known in the art, then when the handles are moved together, through the sequence shown in FIGS. 5 and 6, the posts 27 and 28 move downwardly on the rod or item and thereby form the bend against the resistance to the item as presented by the center post 12.

In that arrangement, the center post 12 is shown to have three different peripheral configurations, namely, 31, 32, and 33, as seen in FIG. 1. These three peripheral configurations 31, 32, and 33, are presented on a cam 34 which is rotatable about the longitudinal axis 21 for presenting the selected one of the cam configurations in the position adjacent the posts 27 and 28, again, as well known in the prior art. The cam 34 is rotatable on the nut 17 by the inter-engaged surfaces designated at 36. To hold the cam 34 yieldingly downwardly, the upper end of the bolt 16 has a reduced shank at 37, and the shank 37 has interior threads, as shown, and there is a bolt 38 which extends in the cam 34 and down to the bolt shank 37 to thread therewith and thereby establish the overall lengths from bolt head 38 to the head of the bolt 16. The cam 34 has a cylindrical opening 39 extending therethrough, and a compression spring 41 is disposed within the opening 39 and is seated between a shoulder 42 on the cam 34 and the head of the bolt 38.

With that arrangement, the cam 34 can be moved longitudinally axially upwardly, as viewed in FIG. 7, and can then be rotated about that axis 21 to one of the selected positions mentioned. The cam 34 has a circular flange 43 extending therearound and overlapping the nut flange 24 and thus enclosing the flange 24. That is, the cam 34 has a circular undercut at 44 for receiving the nut flange 24.

Beyond the aforementioned arrangement with the nut 17 restricting movement along the axis 21, as described and shown, there is a pin 46 which interconnects between the handles 10 and 11 and the cam 34. Thus, the handles 10 and 11 have an elongated slot 47 and 48, respectively, and the pin 46 extends through the two slots 47 and 48 and upwardly for engagement with the cam 34. Therefore, the pin 46 is of sufficient length to engage both of the handles 10 and 11 and also be in direct contact with the cam 34, as best shown in FIG. 7. Cam 34 has three circularly-spaced grooves 49 on its underface 51, as seen in FIG. 12, and those grooves 49 are radially disposed about that longitudinal axis 21 and are faced downwardly for receiving the upper end of the pin 46, in the FIG. 7 display.

With that arrangement, whenever one of the downwardly facing grooves 49 is aligned with the pin 46, then the pin will be disposed within that one groove 49 and thereby hold the cam 34 ill that selected rotated position which was achieved by raising the cam 34 against the downward force of the yielding spring 41 and then permitting the spring 41 to reseat the cam 34 down onto the pin 46 and onto the nut 17, as shown.

FIGS. 4, 5, and 6 show that the slots 47 and 48 are disposed in mirror image about the upright longitudinal plane through those three views, and thus, when the handles 10 and 11 are pivoted, then the slots 47 and 48 will always be overlapping to present one restricted opening therebetween, namely, an opening just adequate in size for receiving the pin 46 and thus guiding the pin 46 radially inwardly and outwardly, relative to the longitudinal axis 21, when the handles 10 and 11 are moved outward and inward, respectively. Therefore, the pin 46 is in direct contact with the handles 10 and 11 and also with the cam 34, and there are no intervening parts or any types of connections required to present the pin 46 to the cam 34 for holding the cam 34 in its selected rotated position throughout the maneuvering of the handles 10 and 11 for the bending process.

Even still further, as seen between FIGS. 4, 5, and 6, the handles are brought into maximum bending position of FIG. 6, then the pin 46 is at its maximum distance from the longitudinal axis 21 and thus the pin 46 is optimally positioned for holding the cam 34 against any undesirable rotation during the bending.

To permit the pin 46 to engage the cam 34 in one of the three slots 49, the nut 17 has a radially extending slot 52 which the pin 46 projects through to extend to the cam 34. Of course the nut 17 is in a fixed rotated position once it is tightened relative to the bolt 16, and thus the slot 52 is always presented in the radial orientation shown.

It will be further noted, in FIGS. 7 and 8, that the pin 46 has an enlarged head 53, and that head 53 is slidably received in the handle slot 47, and thus the slot 47 is slightly wider than the slot 48. Also, the handle 11 has a slot bottom surface 54 which upwardly supports the head 53 and thus establishes the overall extent of the pin 46 toward the cam 34. The extent of the pin 46 and the upward movement of the cam 34 against the spring 41 are arranged so that the cam 34 will clear the pin 46 when the cam 34 is raised, and thus the pin 46 will not then restrict rotation of the cam 34. That is, the dimensioning is critical to permit that type of clearance of the pin 46 for the desired rotation of the cam 34 until the cam 34 is released and the spring 41 moves downwardly to where the pin 46 will engage one of the cam grooves 49, such as in the arrangement shown in FIG. 7.

What is claimed is:

1. In a bending tool of the type comprising a pair of handles, a pivot post having a longitudinal axis and being pivotally connected with said handles to pivotably connect said handles together at the intermediate length of said handles, said handles including hand grips disposed to one side of said axis and bending posts being disposed to the other side of said axis, an adjustable cam having a central longitudinal axis disposed co-axially with said longitudinal axis and being supported by said pivot post for rotation about said longitudinal axis, said cam having a plurality of peripheral surfaces selectively positionable to a position adjacent said bending posts upon rotation of said cam about said longitudinal axis, the improvement comprising a slot in each of said handles adjacent said pivot post and being disposed to have respective portions of said slots overlap each other in an arrangement to form one pin opening extending through said slot portions throughout the pivoting of said handles and with said pin opening having an axis extending through said handles in the direction parallel to said longitudinal axis, said slots being disposed to be eccentric to said longitudinal axis for moving said pin opening axis toward and away from said longitudinal axis upon pivoting of said handles about said longitudinal axis, said cam having grooves thereon extending radially relative to said longitudinal axis and being located to be exposed to said pin opening, and a pin disposed in said pin opening for movement with the movement of said pin opening and extending into a selective one of said grooves for securing said cam in a selective rotated position.

2. The bending tool as claimed in claim 1, including a spring disposed to be interactive between said cam and said pin for yieldingly urging them together into position to have said pin extend into one of said grooves.

3. The bending tool as claimed in claim 2, wherein said spring is disposed to be operative on said cam for yieldingly urging said cam toward said pin.

4. The bending tool as claimed in claim 1, wherein said slots are disposed in mirror image on said handles and with each having an end disposed radially furthest away from said longitudinal axis when said handles a pivoted toward each other.

5. The bending tool as claimed in claim 1, wherein said slots and said pin are arranged to have said pin confined by said slots and thereby move said pin only radially of said longitudinal axis upon pivotal movement of said handles.

6. In a bending tool of the type comprising a pair of handles, a pivot post having a longitudinal axis and being pivotally connected with said handles to pivotally connect said handles together at the intermediate length of said handles, said handles including hand grips disposed to one side of said axis and bending posts being disposed to the other side of said axis, an adjustable cam having a central longitudinal axis disposed co-axially with said pivot post longitudinal axis and being supported by said pivot post for rotation about said longitudinal axes to selected rotated positions, a spring interposed between said post and said cam for yieldingly holding said cam relative to said post, said cam having a plurality of peripheral surfaces selectively positionable to a positions adjacent said bending posts upon rotation of said cam about said longitudinal axis, the improvement comprising a pin operatively interconnected between said handles and said cam and being in direct contact with both said handles and said cam and being arranged for movement in contact with said cam in the direction radially of said longitudinal axes in response to pivoting of said handles for restraining said cam against rotation when in a selected position.

7. The bending tool of the type as claimed in claim 6, wherein said interconnection includes a slot on each of said handles for receiving said pin and with said slots and said pin being arranged to move said pin in said radial direction upon pivoting of said handles in the bending use of said tool.

8. The bending tool of the type as claimed in claim 7, wherein said slots are disposed to be in mirror image relative to each other and to be overlapping in their projected images to thereby present one pin opening extending therethrough for the entrapment and guidance of said pin.

9. The bending tool of the type as claimed in claim 7, wherein said slots are of widths different from each other, and with the one of said slots furthest from said cam being wider in width than the one of said slots nearest to said cam, and said pin has an enlarged head disposed in said wider slot.

10. The bending tool of the type as claimed in claim 7, wherein said slots are disposed on two parallel planes and are angularly disposed with respect to each other and are arranged to move in various positions of overlapping alignment with each other upon pivoting of said handles and thereby form one through-hole for the snug reception of said pin.

\* \* \* \* \*